United States Patent [19]

Erchak et al.

[11] 4,156,101
[45] May 22, 1979

[54] LOW MOLECULAR WEIGHT TERT.-ALCOHOLS

[75] Inventors: Michael Erchak, Ridgewood, N.J.; George E. Cremeans, Groveport; Elmer J. Bradbury, Columbus, both of Ohio

[73] Assignee: Dart Industries Inc., Los Angeles, Calif.

[21] Appl. No.: 453,118

[22] Filed: Mar. 20, 1974

[51] Int. Cl.$^2$ .................. C07C 29/00; C07C 35/02
[52] U.S. Cl. ................................. 568/904; 568/715; 568/834
[58] Field of Search ............... 260/642 R, 642 B; 568/904, 834, 715

[56] References Cited

U.S. PATENT DOCUMENTS

| | | | |
|---|---|---|---|
| 2,402,137 | 6/1946 | Hanford et al. | 260/642 R |
| 2,409,683 | 10/1946 | Howk et al. | 260/642 R |
| 2,668,181 | 2/1954 | Banes et al. | 260/642 R |
| 2,713,071 | 7/1955 | Erchak | 260/642 R |
| 2,717,910 | 9/1955 | Erchak | 260/642 R |
| 2,833,808 | 5/1958 | Brendlein et al. | 260/642 R |
| 3,100,792 | 8/1963 | Emrick | 260/642 R |
| 3,213,149 | 10/1965 | Takahashi et al. | 260/642 R |
| 3,255,260 | 6/1966 | Anderson | 260/642 R |

FOREIGN PATENT DOCUMENTS

| | | | |
|---|---|---|---|
| 244066 | 1/1960 | Australia | 260/642 R |
| 685896 | 5/1964 | Canada | 260/642 R |

*Primary Examiner*—Joseph E. Evans
*Attorney, Agent, or Firm*—Margareta LeMaire; Bryant W. Brennan; Harold R. Beck

[57] ABSTRACT

Process for the telomerization of olefins with secondary alcohols comprising admixing a secondary alcohol telogen with a mono-olefinically unsaturated hydrocarbon taxogen in catalytically effective amounts of a free radical generating initiator in a reaction zone, the telogen to taxogen molar ratio in the reaction zone being greater than about 1:1 as measured on the effluent stream from the reaction zone, at a temperature ranging from about 125° C. to about 275° C. and that a pressure varying from about 2000 psi to about 10,000 psi.

10 Claims, No Drawings

LOW MOLECULAR WEIGHT TERT.-ALCOHOLS

This invention relates to a process for telomerizing olefins with secondary alcohols. More particularly, this invention relates to the telomerization of olefins with secondary alcohols to obtain low molecular weight tert.-alcohol telomers characterized by at least 60% and preferably more than 80% by weight of the product distribution exhibiting a boiling point less than about 245° C. at a vacuum of about 0.5 mm Hg. These temperature and pressure conditions correspond to a telomer containing about 10 to 12 taxogen units per telogen unit, depending on the molecular weight of the initial telogen unit.

The term "telomerization" has been used to designate a type of reaction which can be represented as follows:

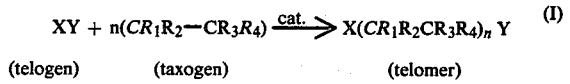

(telogen)   (taxogen)   (telomer)

The compound XY, which supplies the end groups of the product molecule, is called a "telogen" or "chain transfer agent", and the polymerizable olefinic monomer is called a "taxogen". The product is a mixture of "telomer" molecules of different chain lengths. Further information and a bibliography of literature on reactions of this type are obtainable from the publication, "Telomerization, A Review of the Literature," U.S. Department of Commerce, Office of Technical Services, PB 131930, dated Nov. 19, 1958, which publication also serves to illustrate the classes of compounds that can be used as telogens and taxogens in the process of the present invention.

It is also known that this reaction is greatly dependent on the reactivity of the telogen (chain transfer agent) used. Mayo (JACS, 65, 2324(1943) has shown that the degree of polymerization $D_p$ at low conversion of monomer to polymer in a free-radical polymerization can be represented by the equation:

$$1/D_p = (1/D_{po}) + C_s([T]/[E])$$

where $D_p$ is the number-average degree of polymerization ($\overline{M}_n$ divided by monomer molecular weight), [T] is the initial telogen molar concentration, [E] is the initial monomeric taxogen molar concentration; $C_s$ is the chain-transfer constant, and $D_{po}$ is the degree of polymerization in the absence of a chain-transfer agent. In the case of low molecular weight telomers, it has also been found necessary to subtract the molecular weight of the telogen from $\overline{M}$. Chain-transfer constants have been computed for a variety of systems by experimental methods. (See, for example, Tidwell and Mortimer, J. Poly. Sci., Part A-1, 8, 1549 (1970)).

Although all telogens exhibit varying degrees of reactivity, only a few have been found useful in the preparation of products where n (equation I, supra) is below 12. Thus, telogens (such as t-butanol) having low reactivities, i.e., low chain transfer constants, require the use of excessive amounts of initiators along with large amounts of telogen in comparison with the amount of olefin. On the other hand, telogens such as isopropanol are over 100 times more reactive.

Another factor of great significance is by-product formation. It is known that telomerization reactions generally yield complex mixtures of products which vary in molecular weight as well as functional complexity. For example, the reaction of an ester, such as methyl acetate ($CH_3COOCH_3$) with ethylene will yield the corresponding normal and branched alkanoates as well as varying amounts of branched fatty acetates. Simultaneously, large amounts of the corresponding branched, higher molecular weight esters will also be formed. This is due to the fact that the ethylene chain growth can occur on both $CH_3$ groups, ultimately replacing all of the six hydrogens. Such reactions, though well known, have little to no commercial value.

Similarly, initiator efficiency is an important factor. Conventional polymerization systems used in the manufacture of polyethylene, polystyrene or the like generally have very high initiator efficiency. However, in the preparation of low molecular weight products (below $C_{24}$) large amounts of initiator are required—in the order of at least 200 times more catalyst is required. The use of such large amounts of catalyst results in prohibitive raw materials costs and economically unattractive processes.

It is also known that the use of higher temperatures in telomerization reactions favor the obtainment of lower molecular weight. Unfortunately, in most cases higher temperatures tend to cause side reactions—thus increasing the number of by-products. In addition, decomposition frequently occurs with subsequent formation of undesirable by-products. For this reason, temperature control has not been successfully used in low molecular weight telomerization synthesis.

In the case of ethylene telomerization, effective control of molecular weight generally requires the use of low pressures. This, in turn, also leads to excessive use of initiators as well as concurrent formation of by-products and, therefore, is commercially unattractive.

Ethylene-alcohol telomers were first described in the Hanford et al. patent, U.S. Pat. No. 2,402,137. These materials are described as ranging from soft greases to hard waxy products exhibiting specific melting point ranges and have average ethylene to telogen molar ratios ranging from 20:1, and generally from 30:1, although the ethylene chain can be considerably longer. Although the chemical structure of these telomers is such that they potentially could be useful chemical intermediates, this potential has not been realized to any significant extent for over 25 years primarily because the molecular weight range of the telomers obtained by said process is too high.

Accordingly, it is the object of the present invention to provide olefin-secondary alcohol telomers characterized by at least 60% and preferably more than 80% by weight of the product distribution exhibiting a boiling point less than about 245° C. at 0.5 mm Hg. Such telomers generally exhibit an olefin/secondary alcohol molar ratio of less than 12.

It is another object of the present invention to provide a process for the preparation of tert.-alcohol telomers.

These, as well as other objects, are accomplished by the present invention which provides a process for the telomerization of olefins with secondary alcohols comprising admixing a secondary alcohol telogen with a mono-olefinically unsaturated hydrocarbon taxogen and catalytically effective amounts of a free radical generating initiator in a reaction zone, the telogen to taxogen molar ratio in the reaction zone being greater than about 1:1 as measured on the effluent stream from the reaction zone, at a temperature ranging from about 125° C. to about 275° C. and at a pressure varying from about 2000 psi to about 10,000 psi.

The process can be typically illustrated by the telomerization of ethylene with isopropanol as follows:

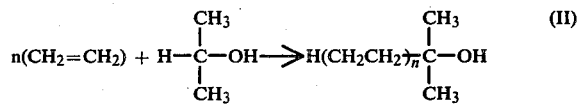

As employed herein, the term "secondary alcohol" is intended to encompass all secondary alcohols which have the general structure:

wherein $R_1$ and $R_2$ are $C_1$–$C_8$ alkyl or phenyl radicals which can be the same or different or which conjointly form a polymethylene bridge. Illustrative alcohols include, for example, isopropyl alcohol, butanol-2, pentanol-2, cyclohexanol, diethyl carbinol, methyl n-propyl carbinol, and the like.

The main objective of this telogen structure is that it is highly directive as to where chain transfer will occur, and that it is substantially more reactive as a chain transfer agent than the resultant telomer that is formed thereby minimizing long chain branching. It is also recognized that each secondary alcohol telogen will have a different chain transfer constant $C_s$ with an olefin at some reference temperature and pressure condition, depending on its structure. Therefore, a specific reactant telogen/taxogen (T/E) ratio is not applicable to all alcohol telogens to obtain a given degree of polymerization. As noted in Mayo's equation, supra, the degree of polymerization ($D_p$), the average number of monomer units per chain, is specifically related to the chain transfer constant $C_s$ and the telogen/taxogen (T/E) molar ratio. In general, tertiary hydrogens are more reactive than secondary hydrogens which, in turn, are more reactive than primary hydrogens. Thus, by selecting the structures of $R_1$ and $R_2$ (formula III), the desired object of the telogen effect may be met.

The preferred type of secondary alcohol is an alcohol wherein $R_1$ and/or $R_2$ is a methyl, tert-butyl, phenyl, or any other like structure which has no significantly reactive hydrogen.

The mono-olefinically unsaturated hydrocarbons employed as the taxogen in this invention can be represented by the formula:

$$H_2C=CHR \qquad (IV)$$

wherein R can be hydrogen, $C_1$–$C_8$ alkyl and phenyl. Illustrative of such taxogens are ethylene, propylene, 4-methylpentene-1 styrene and the like. Most preferably, the taxogen is ethylene.

It has been found in accordance with the present invention that by maintaining the reactant telogen/taxogen molar ratio above about 1:1, telomer products can be obtained wherein the average taxogen/telogen molar ratio in the product is less than about 12:1 in the principal fraction. It is considered preferable that the reactant telogen/taxogen molar ratio range from about 3:1 to about 20:1. The average molecular weight of the product will decrease as the reactant telogen/taxogen ratio is increased, the temperature is increased and/or the pressure is decreased. However, there is an upper temperature, generally around 300° C., where excessive undesired side reactions occur and a minimum pressure, generally around 2000 psi depending upon available reaction time, where excessive initiator usage and product unsaturation occurs. Thus, the reactant telogen/taxogen molar ratio becomes the main operating variable to achieve the low average molecular weight telomers of the present invention.

The telomerization reaction is effected in the presence of a free radical generating initiator. Typically, peroxides or azo initiators are employed. Suitable initiators include di-tertiary butyl peroxide, cumene hydroperoxide, paramenthane hydroperoxide, dicumyl peroxide, tertiary butyl hydroperoxide, tertiary butyl peracetate, cyclohexanone peroxide, decanoyl peroxide, lauryl peroxide, diisopropylperoxydicarbonate, 2,2'-azobis (isobutyronitrile), and hydrogen peroxide. Oxygen in low concentrations can also be used as is well known in the ethylene polymerization art. Ditertiary butyl peroxide is particularly preferred, since its useful half life range fits a desirable temperature range, especially for a continuous reaction, and minimal residues thereof are found in the telomer product.

A catalytically effective amount of the free radical generating initiator is required to initiate the reaction. Generally, about $1 \times 10^{-5}$ to about $5 \times 10^{-2}$ moles of initiator per mole of telogen can be suitably employed.

If desired, although not considered necessary, an initiator activator can be additionally employed to enhance the initiator activity. However, this is basically an economic objective where lower cost, high temperature initiators may be more effectively used in a lower temperature region. The activators have no effect on molecular weight control unless they are effective chain transfer agents and thus contained in the desired telomer product. Typical initiator activators include ferrous salts such as ferrous chloride, amines such as dimethylamine, pyridine and the like, mercaptans such as the fatty amine mercaptans such as lauryl mercaptans, cobalt naphthenate and the like. Azobisisobutyronitrile has also been found useful in conjunction with peroxide initiators in providing decomposition at lower temperatures.

In practice, it has been found that the reaction can be conducted under essentially batch, semi-continuous or continuous conditions. It is considered preferable, however, to employ semi-continuous or continuous techniques. This is because the batch method engenders a large free radical concentration gradient as the reaction proceeds and broadens the molecular weight distribution during the course of producing a satisfactory yield of telomer reducing the yield of the desired molecular weight range. Continuous reaction is readily effected by maintaining essentially constant instantaneous flow rates on the inlet and outlet process streams of an agitated autoclave, and analyzing the reactor exit stream for the telogen/taxogen (T/E) molar ratio. As long as sufficient mixing occurs during the initiator half life period, (usually two or more turnovers of reactants per half life period is considered adequate), the concentration gradients are considered adequate. It is recognized that increasing the T/E ratio requires an increase in the reactor residence time to maintain an equivalent wt. % conversion.

The objective in the semi-continuous method is to maintain a low free radical concentration gradient by multiple additions of very small quantities of initiator (for example, about 1/10–1/20 of the total initiator required per addition). The additions can be made at a frequency that is equivalent to three or four half life periods of the initiator used. The frequency, however, is not as critical as the concentration level of each addition. The addition quantity should not produce much more than about one percent conversion per addition based on the total weight of the reactor contents or weight percentage of the reactor exit stream.

The telomerized products of the present invention, i.e. tert.-fatty alcohols, are useful, per se, and can be readily converted to fatty acids or terminally unsaturated hydrocarbons by any of several well-known chemical methods.

For example, the tert.-fatty alcohols can be converted to fatty acids by oxidation with air or another oxidizing agent. Preferably said alcohols can be oxidized with air in either batch, semi-continuous or continuous fashion. In a batch system, the t-fatty alcohols, either as crude mixtures or as narrow distillation cuts, can be introduced into a suitable reactor, e.g.; a stirred autoclave, along with a suitable solvent such as acetic acid or the like containing small amounts of a metallic catalyst, e.g., copper and/or manganese acetate. The reaction mixture can then be heated to about 70°–80° C. and air introduced through a sparger for a period of several hours while maintaining a pressure of about 100 psig. Spent air can be removed from the top of the reactor continuously while fresh air (diluted with nitrogen, if necessary) is introduced into the bottom. A reflux condenser is provided to recover reactants from the off-gas. At the end of the reaction, as indicated by analysis, the reactor can be depressurized and the contents discharged for further processing.

In a continuous process, two types of reactors can be used bubble (trickle) phase type or foam-phase type. Air (alone or diluted with nitrogen) can be introduced at pre-selected rates depending on the degree of conversion required. Usually higher air feed rates are used in foam-phase systems. Temperatures are generally maintained at about 80°–120° C. and pressure at from about atmospheric to about 100 psi. Residence time can vary from about 1 to about 20 hours and will vary depending on the desired degree of conversion per pass. Generally, the percent conversion is dictated by the purity of the reaction products being obtained.

The crude oxidized product from either the batch or the continuous reactor can be collected and neutralized, for example, with caustic soda or a solution of sodium carbonate and sodium hydroxide; the resulting fatty acid soaps can then be separated from un-oxidized starting material by centrifuging, filtration, decanting, and the like. Undesired keto and hydroxy acids, if present, can be decomposed by heat treatment. Alternatively, the crude oxidized product can be neutralized with ammonia and subsequently decomposed to form fatty acids and ammonia for recycle. It may also be preferable to simply react the sodium or ammonium soaps by acidifying with sulfuric acid. The byproduct, sodium sulfate or ammonium sulfate, can be isolated and sold as a byproduct. If desirable, it is, of course, possible to subject the crude fatty acid reaction mixture to simple distillation in order to remove low molecular weight acids such as acetic acid and formic acid—prior to neutralization, and subsequent recovery of fatty acids. These can be further purified by simple distillation procedures. Unreacted tert.-fatty alcohol feed-stocks can be returned to the reactor and recycled.

The tert.fatty-alcohols of this invention also can be readily converted to alkenes using well-known dehydration methods. A great variety of dehydrating agents have been employed in the widely used synthesis of alkenes from alcohols. Among the most common are acids, such as sulfuric, anhydrous or aqueous oxalic, or phosphoric; acidic oxides such as phosphorus pentoxide; bases such as potassium hydroxide, and salts such as sodium or potassium acid sulfate; and iodine, dimethyl sulfoxide, phenyl isocyanate, N-bromosuccinimide in pyridine or phosphorus oxychloride, thionyl chloride and the like.

Alternatively, the tert. fatty alcohols can also be dehydrated satisfactorily by passing them or their vapors over alumina at elevated temperatures of about 300°–400° C. Other dehydration catalysts than alumina can be used, e.g., thorium oxide, glass beads, glass beads coated with thorium oxide, clay and silica gel. In practice, dehydration is carried out by simply passing the tert.fatty alcohols over a catalyst bed maintained at about 350°–500° C. under slight vacuum (100–200 mm. Hg). The condensate is collected, dried, and distilled. Conversion yields are generally very high—essentially quantitative.

The following examples further illustrate the present invention. Unless otherwise stated, all percentages and parts are by weight.

EXAMPLE 1

An 850 cc. stainless steel bomb was purged with nitrogen, then with ethylene, and charged with 315 grams of isopropanol. The vessel was then closed, placed in a rocker assembly, connected to an ethylene supply, given three additional low pressure ethylene purges, pressurized with ethylene to about 1,000 psi, and heated while rocking to about 200° C. During the heating period, additional ethylene was added and the pressure adjusted to reach 4,000 psi. At this point, 0.65 grams of cumene hydroperoxide dissolved in 30 cc of isopropanol was injected into the reactor and ethylene pressure increased to 5,000 psi. This pressure was maintained for a period of six hours. The isopropanol to ethylene molar ratio during the reaction was about 1.32.

After termination of the reaction period, heating was discontinued and the assembly allowed to cool to room temperature. The cold vessel was then removed, weighed and depressurized to remove unreacted ethylene. The vessel was then opened and the reaction mixture discharged and filtered to remove solids. The yield of solid product was 5.1 grams. The filtrate was then distilled in order to remove unreacted isopropanol. Approximately 22.4 grams of liquid product was thus obtained. Total yield of product was 27.5 grams.

Molecular weights were determined using both Gel Permeation and Gas Phase Chromatograph (GPC) methods. The molecular weight of the liquid portion was found to be in the range of 200–238 and the solid portion about 470. The average molecular weight for the entire product was estimated to be in the range 228–350. The GPC spectra showed that the product was particularly clean in that only one major component, representing 80–90% of the total, was found for each two carbon unit. Distribution of the product was fairly uniform over the $C_{11}$ to $C_{27}$ range. Infrared (IR) examination of the liquid portion revealed definite presence of OH and methyl groups.

Conversion of isopropanol/ethylene telomer to fatty acids was accomplished by the following oxidation procedure:

A small sample of the liquid product (0.5 grams) was added to 10 ml of an oxidizing solution containing 50% nitric acid and 0.1% ammonium vanadate. The mixture was heated at 80° C. for 60 minutes, cooled and treated immediately with a buffered salt solution (200 ml of 4% sodium carbonate; 4% sodium bicarbonate; 10% sodium chloride). The solution was then extracted with methylene chloride to remove soluble impurities and unoxidized telomer. The water soluble sodium salts of fatty acids remaining in the water layer were converted to acids by addition of HCl to a pH of 3.0. The fatty acids thus obtained were dissolved by extraction with two ml portions of methylene chloride. These were combined and dried over anhydrous magnesium sulfate. IR studies were made by evaporating the solvent from the salt plates. Examination of the IR data revealed definite presence of fatty acids spectra.

EXAMPLE 2

This example illustrates the importance of maintaining the T/E ratio at at least about 1.0 in order that at least 60% of the product distribution exhibit a boiling point less than 245° C. at 0.5 mm Hg.

In this example, the procedure used in Example 1 was repeated with the exception that isopropanol was decreased from 315 grams to 225 grams, giving a telogen to ethylene (T/E) ratio of 0.70. The amount of product formed was 21 grams of which 57% was liquid and the rest solid. The molecular weight as determined by GPC was found to be in the range of 400-500. The molecular weight of the liquid portion was in the range 310-392. IR analysis revealed distinct presence of OH and methyl groups as in previous products.

EXAMPLE 3

In this example, the procedure followed in Example 1 was repeated with the exception that cyclohexanol was substituted for isopropanol. Paramenthane hydroperoxide was used as the catalyst and the reaction was conducted at 165° C. and 6,000 psi. T/E ratio was 5.7. On working up the reaction mixture as described in Example 1, 27.8 grams of product was isolated. Molecular weight of this material was found to be 257 by the GPC method. Infrared analysis revealed distinct presence of OH and indicated complete absence of other functional groups.

EXAMPLE 4

Conversion of isopropanol/ethylene telomer to the corresponding alkenes was accomplished by the following dehydration procedure:

A small sample of the liquid product (0.5 grams) was vaporized and passed over an alumina catalyst bed maintained at about 425° C. under a vacuum of about 150 mm. Hg. The condensate was collected, dried and distilled. Conversion was essentially quantitative. Examination of IR data revealed definite presence of terminal unsaturation.

What is claimed is:

1. Process for the telomerization of olefins with secondary alcohols to obtain low molecular weight tert.-alcohol reaction product most of which exhibits a boiling point of less than 245° C. at 0.5 mm Hg pressure comprising admixing a secondary alcohol telogen represented by the structural formula:

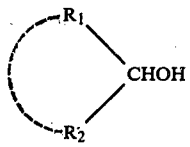

wherein $R_1$ and $R_2$ are $C_1$-$C_8$ alkyl or phenyl radicals which can be the same or different or which conjointly form a polymethylene bridge with a mono-olefinically unsaturated hydrocarbon taxogen having the structural formula:

$$H_2C=CHR$$

wherein R can be hydrogen, $C_1$-$C_8$ alkyl or phenyl in the presence of catalytically effective amounts of a free radical generating initiator selected from the group consisting of an organic peroxide, an azo-type initiator and oxygen, and in the presence of an initiator activator selected from the group consisting of ferrous salts, amines, mercaptans and cobalt naphthenate in a reaction zone at a temperature between about 125° C. and about 275° C. and at a pressure between about 5000 psi and about 10,000 psi, the telogen to taxogen molar ratio in the reaction zone being substantially higher than 1:1.

2. Process as defined in claim 1 wherein the telogen/taxogen molar ratio ranges from about 3:1 to about 20:1.

3. Process as defined in claim 1 wherein the free radical generating initiator is di-tertiary butyl peroxide.

4. Process as defined in claim 1 wherein the free radical generating initiator is employed in amounts of from $1 \times 10^{-5}$ to about $5 \times 10^{-2}$ moles of initiator per mole of telogen.

5. Process as defined in claim 1 wherein an organic peroxide initiator is employed in conjunction with azobisisobutyronitrile.

6. Process as defined in claim 1 conducted under semi-continuous conditions.

7. Process as defined in claim 1 conducted under continuous conditions.

8. Process as defined in claim 6 wherein a low free radical concentration gradient is maintained within the reaction zone by a plurality of additions of from about 1/10 to about 1/20 of the total initiator required per initiator addition.

9. Process as defined in claim 1 wherein the mono-olefinically unsaturated hydrocarbon taxogen is ethylene.

10. Process as defined in claim 1 wherein the secondary alcohol telogen is isopropanol.

* * * * *